(12) United States Patent
Grecu et al.

(10) Patent No.: US 10,213,104 B2
(45) Date of Patent: Feb. 26, 2019

(54) EYE POSITION REGISTERING AND TRACKING

(71) Applicant: Alcon Pharmaceuticals Ltd., Fribourg (CH)

(72) Inventors: Horia Grecu, Berlin (DE); Ralf Weise, Berlin (DE)

(73) Assignee: Alcon Pharmaceuticals, Ltd., Fribourg (CH)

( * ) Notice: Subject to any disclaimer, the term of this patent is extended or adjusted under 35 U.S.C. 154(b) by 857 days.

(21) Appl. No.: 14/065,173

(22) Filed: Oct. 28, 2013

(65) Prior Publication Data

US 2014/0049750 A1  Feb. 20, 2014

Related U.S. Application Data

(63) Continuation of application No. 13/250,873, filed on Sep. 30, 2011, now Pat. No. 8,591,030, which is a continuation of application No. 10/499,498, filed as application No. PCT/EP02/14735 on Dec. 23, 2002, now Pat. No. 8,048,065.

(60) Provisional application No. 60/343,409, filed on Dec. 12, 2001.

(51) Int. Cl.
| | |
|---|---|
| *A61B 18/18* | (2006.01) |
| *A61B 3/10* | (2006.01) |
| *A61B 3/113* | (2006.01) |
| *G06K 9/00* | (2006.01) |
| *A61F 9/008* | (2006.01) |

(52) U.S. Cl.
CPC .......... *A61B 3/113* (2013.01); *A61F 9/00804* (2013.01); *G06K 9/00597* (2013.01); *A61F 9/008* (2013.01); *A61F 2009/00846* (2013.01); *A61F 2009/00872* (2013.01)

(58) Field of Classification Search
CPC ... A61B 3/10; A61B 3/11; A61B 3/113; A61F 9/008; A61F 9/00802; A61F 9/00804; A61F 2009/00844; A61F 2009/00846
USPC ........ 351/5, 9–12; 606/4–6, 10–12; 128/898
See application file for complete search history.

(56) References Cited

U.S. PATENT DOCUMENTS

| | | | |
|---|---|---|---|
| 4,856,891 A * | 8/1989 | Pflibsen | A61B 3/113 351/206 |
| 5,098,426 A | 3/1992 | Sklar et al. | |
| 5,129,400 A * | 7/1992 | Makino | A61B 3/1225 351/206 |

(Continued)

FOREIGN PATENT DOCUMENTS

WO   WO 02/064031   8/2002

OTHER PUBLICATIONS

International Search Report and Written Opinion issued for PCT/EP2002/14735 dated Jun. 10, 2003, 2 pgs.

(Continued)

*Primary Examiner* — Ahmed Farah

(57) ABSTRACT

Embodiments of the invention refer to a system for registering and tracking the position of a person's eye, in particular for refractive ophthalmic surgery. According to embodiments, the system is structured such that eye images containing at least the iris and the pupil of the eye are made at a first wavelength of light and that eye images containing scleral blood vessels are made at a different second wavelength of light. The invention furthermore refers to a corresponding method for registering and tracking the position of a person's eye.

1 Claim, 11 Drawing Sheets

(56) References Cited

U.S. PATENT DOCUMENTS

| | | | |
|---|---|---|---|
| 5,331,149 A * | 7/1994 | Spitzer | A61B 3/113 |
| | | | 250/221 |
| 5,345,281 A | 9/1994 | Taboada et al. | |
| 5,844,658 A * | 12/1998 | Kishida | A61B 3/1241 |
| | | | 351/206 |
| 6,099,522 A | 8/2000 | Knopp et al. | |
| 6,283,954 B1 * | 9/2001 | Yee | A61F 9/008 |
| | | | 351/210 |
| 6,491,687 B1 | 12/2002 | Sumiya et al. | |
| 6,634,749 B1 | 10/2003 | Morrison et al. | |
| 7,480,396 B2 * | 1/2009 | Teiwes | A61B 3/113 |
| | | | 351/206 |
| 8,048,065 B2 * | 11/2011 | Grecu | A61B 3/113 |
| | | | 128/898 |
| 8,801,183 B2 * | 8/2014 | Shahidi | A61B 3/1241 |
| | | | 351/206 |
| 2002/0008848 A1 * | 1/2002 | Ono | A61B 3/145 |
| | | | 351/209 |
| 2009/0275929 A1 * | 11/2009 | Zickler | A61B 3/113 |
| | | | 606/5 |

OTHER PUBLICATIONS

Mulligan, Jeffrey B., "Image Processing for Improved Eye-Tracking Accuracy", Behavior Research Methods Instruments & Computers, Feb. 1997, pp. 54-65, vol. 29, Issue 1.

* cited by examiner

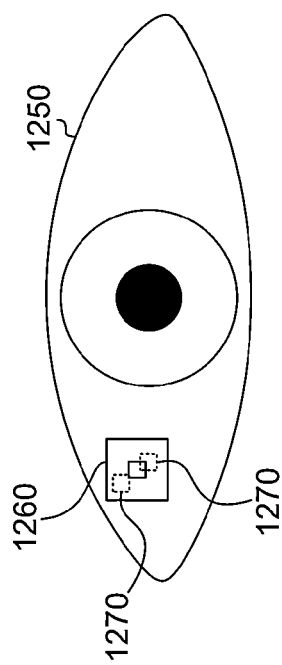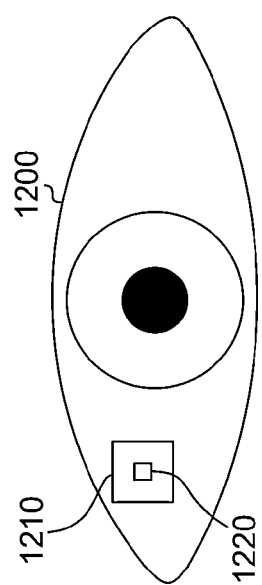
FIG. 7

EYE POSITION REGISTERING AND TRACKING

CROSS REFERENCE TO RELATED APPLICATIONS

This application is a continuation of U.S. patent application Ser. No. 13,250,873, filed Sep. 30, 2011, now allowed, which is a continuation of U.S. patent application Ser. No. 10/499,498, filed on Dec. 23, 2002, now U.S. Pat. No. 8,048,065, which is a 371 Application of PCT/EP02/14735, filed Dec. 23, 2002, which claims benefit of U.S. Provisional Application 60/343,409, filed Dec. 21, 2001, the disclosures of all of which are herein incorporated by reference.

BACKGROUND

This disclosure relates to a system for registering and tracking the position of a person's eye, in particular for refractive ophthalmic surgery, comprising:
 a camera system (18) for taking images of the person's eye;
 storage means connected to the camera system (18) for storing at least one eye image as a reference eye image;
 an image processing system connected to the storage means and the camera system (18) for comparing a momentary eye image with the reference eye image and for outputting a signal representing a change of eye position between the reference eye image and the momentary eye image.

Such systems are e.g. used in refractive ophthalmic surgery, i.e. in surgical operations in which the cornea of a patient's eye is shaped by a laser beam in order to correct for defects of vision. Before the surgical operation, a measurement of the patient's eye is made with the patient usually sitting in an upright position while focussing on a target image. A so-called wavefront analyzer or other refractive diagnostic device, such as corneal topographer or refractometer, then objectively determines an appropriate wavefront correction for reshaping the cornea of the eye. Typically the wavefront analyzer calculates a cylindrical or quasi-cylindrical ablation profile, which is to be applied to the eye by means of a focussed laser beam.

During the refractive surgery operation, the patient usually lies on his back, i.e. his head is typically in another position than during diagnosis with the wavefront analyzer. In order to correctly apply the previously calculated ablation profile to the eye, it is therefore essential to correctly register the position of the person's eye, i.e. to determine the translational and rotational displacement of the eye with respect to its position during diagnosis, so that the system "knows" how to apply the previously calculated ablation profile to the cornea in its momentary position.

Not only changes of eye position between diagnosis and surgery, but also eye movements during the operation have to be taken into account. In refractive laser systems, the laser operates in fixed space coordinates. The patient's eye is classically stabilized by voluntary visual fixation of a visual target. However, eye movements cannot be eliminated completely by voluntary fixation and furthermore slower head movements still occur during the surgery procedure, both changing the eye's position relative to the laser. However, with the increasing demands of customized corneal ablation, in particular the use of smaller beam sizes, faster repetition rates and greater precision of correction, exact positioning of each single laser shot onto the eye has become increasingly more important. This need for greater positioning accuracy has provided the impetus for several refractive laser companies to implement eye tracking systems into their surgical systems in order to position the ablation beam accurately onto the corneal surface and to compensate for patient head and eye movements during the operation. Many eye tracking systems track the image of the pupil. However, the exact position of this image depends on the refraction of light through the cornea in front of the pupil. The amount of corneal tissue through which the light passes may change due to the orientation of the eye, leading to an artificial shift of the image position, which negatively affects the tracking.

When markers are applied to the eye and tracked instead of or in addition to the pupil, other problems arise: The markers may irritate the eye or require anesthesia. In other cases, the attachment of the markers to the patient's eye may not last much longer than for example one hour, therefore imposing a time limitation to the operation and permissible time between refractive measurement and correction Document WO 01/78584 A2 discloses a system for registering and tracking the position of a person's eye according to the preamble of claim 1. For registering purposes, this system compares the limbus centers of the eye in the reference eye image corresponding to its position during diagnosis and in the momentary eye image, and calculates a translational displacement of the eye from the difference of the limbus centers. Furthermore, the position of other eye features like e.g. retinal blood vessels, scleral blood vessels or a retinal nerve are compared between the reference image and the momentary image in order to determine the rotation of the eye between its diagnosis position and its surgery position.

In this prior art system, the eye is basically illuminated by daylight, and the cameras used to take pictures of the eye are "ordinary" cameras for collecting color images. All eye features necessary for registering are therefore visible in each image. However, as all eye features are always illuminated by daylight, the contrast in particular of blood vessels is poor. The registering setup described in the above prior art document, however, is too slow for use in a clinical situation in which longer operation times result in less income, in particular due to the fact that the poor contrast of the essential eye features in all color images renders the localization of these features time-consuming.

Another limitation of the prior art system is that it does not differentiate between blood vessels that are stable relative to the eye (cornea) and vessels which are stable relative to the head. As it is possible for the patient's eye to rotate independently of the head, this leads to some vessels moving relative to the cornea (surgical target area) at varying rates. Blood vessels may move at different rates depending on the relationship between rotation of the head, rotation of the eye, depth of the vessel in the conjunctive or sclera and position of the vessel relative to the eye lids or cornea. Therefore the above described method may result in incorrect or inaccurate results, due to the non-differentiation between vessels that move with the eye, and vessels that move with the head.

It is therefore an advantage of the invention to provide a faster, more accurate system for registering and tracking the position of a person's eye.

According to some embodiments, this advantage is achieved by a system that allows images of the iris/pupil region of the eye to be taken at a different wavelength of light than images of the scleral blood vessels, so that both wavelengths can be set to suitable values in order to enhance the contrast of the respective eye feature.

As an example, in an embodiment of this system according to the invention the first wavelength lies in a wavelength range between preferably 810 nm and 880 nm, but can be also between 780 nm and 950 nm and the second wavelength lies in a wavelength range between preferably 520 nm and 570 nm but can also be 500 nm and 580 nm. In this case, the first wavelength corresponds to infrared (IR) light, which is known to be very suitable for enhancing the iris/pupil contrast. The second wavelength corresponds to green light enhancing the contrast of blood vessels.

In order to further increase the contrast of the scleral blood vessels, the second wavelength can be set to a local maximum of an absorption spectrum of hemoglobin. As is well known, this maximum lies at a wavelength of approximately 550 nm, corresponding to green light.

In order to produce the two kinds of images with different wavelengths, an embodiment of the system according to the invention comprises a first light source system illuminating the iris and the pupil of the eye and a second light source system illuminating the sclera of the eye. In this case, the first light source system emits light of the first wavelength, whereas the second light source system emits light of the second wavelength.

As to the question how these two light source systems co-operate and how the two kinds of images are made with light of different wavelengths, various approaches are conceivable:

In one embodiment of the system according to the invention, the first and second light source systems are controlled such as to simultaneously illuminate the respective parts of the eye. In this case, the patient's eye is simultaneously illuminated with light of two different wavelengths arriving from two different light source systems: The central part of the eye, namely pupil and iris are illuminated with a focussed IR beam, whereas the sclera of the eye is simultaneously illuminated with green light.

At least as far as eye tracking during a surgical operation is concerned, it can be assumed that the amplitude of eye movements is sufficiently small to make sure that no misalignment problems regarding this spatially structured arrangement of light sources will occur. Both light source systems can therefore be stationary. The spatial emission profile of the IR light source system then basically corresponds to a light cone having a diameter of approximately 10 to 11 mm, making sure that no IR light reaches the eye outside the limbus. In a similar way, the light emission profile of the second light source system must be designed such as to make sure that no green light of the second wavelength falls on the iris and pupil.

A particularly flexible adjustment of the spatially structured beams from the two light source systems can be obtained when the system according to the invention furthermore comprises light directing means for variably directing the light of the first light source system and/or the second light source system to the respective parts of the eye. As preferable examples of such light directing means, a scanning mirror and/or a movable lens can be mentioned. The use of such optical devices for precisely directing light beams on a target, in this case the region inside or outside the limbus, is well-known and will therefore not be described in detail.

As an alternative to the above-discussed example of a system using a spatially structured beam, another embodiment can comprise multiplexing means for controlling the first and second light source systems such as to alternately illuminate the entire eye. In other words, such an embodiment does not use spatially structured beams, but rather two separate larger beams of different "color" which are structured in time. As an example, the multiplexing means can choose the first light source system at first, so that the entire eye is illuminated with IR light. The camera system takes a momentary IR image of the entire eye, in which in particular the iris/pupil region has a strong contrast and in which almost no blood vessels are visible. This momentary IR image can be stored in the storage means. Then the multiplexing means switch from the first to the second light source system which then illuminates the entire eye with green light. Again a momentary image of the entire eye is made, in which in particular the blood vessels have a strong contrast. This image can also be stored in the storage means. The image processing system can then calculate any translational displacement of the eye with respect to the reference image based on the IR image of the eye allowing a precise localization of the pupil. Then a possible rotation of the eye with respect to the reference image can be calculated based on the green image allowing a precise localization of the scleral blood vessels.

In yet another embodiment of the invention, the image processing system is designed such as to subtract an image which is recorded at the second wavelength of light from the second light source system from a preceding image recorded at the first wavelength of light from the first light source system. The remaining "difference image" is even more dominated by the scleral blood vessels than the second image itself, which still enhances the precision of the blood vessel localization.

In view of a suitable pupil/iris contrast, the first light source system can be arranged such as to illuminate the eye at an angle of approximately 30° with respect to the visual axis. In particular an illumination of the iris and pupil from approximately 30° below the visual axis has turned out to be suitable in practical operation.

Whereas the first light source system, which basically has to produce one single IR light cone, can consist of a single IR light source, realization of the second light source system is more difficult, as it has to illuminate two separate regions of the eye, namely the sclera on the left and right side of the iris. In an embodiment of the invention suitable for fulfilling this illumination requirement regarding the second wavelength light, the second light source system comprises two light sources arranged such as to symmetrically illuminate the eye at angles of approximately +35° and −35°, respectively, with respect to the visual axis.

In order to further improve the quality of the images made, i.e. to enhance the contrast of the pupil/iris in the IR images and the contrast of the scleral blood vessels in the green images, additional measures can be taken in view of the camera system: Thus, in an embodiment of the invention, the camera system can be only sensitive to light of the first and the second wavelength. In this case, daylight in the operating room does not negatively affect the images.

In practice such an arrangement can be obtained when the camera system comprises one single camera provided with a double-passband filter. Alternatively the camera system can comprise a CCD camera having a combination chip with at least two separate color bands corresponding to the first and the second wavelength, respectively.

As yet another alternative, the camera system can comprise a first camera sensitive only to the first wavelength and a second camera sensitive only to the second wavelength.

Embodiments of the invention furthermore relate to a method of registering and tracking the position of a person's eye, in particular for refractive ophthalmic surgery, comprising the steps:

recording an image of the person's eye in a reference position;

storing the image as a reference eye image;
recording at least one momentary eye image;
calculating a change of eye position between the reference eye image and the at least one momentary eye image; and
outputting a signal representing the change of eye position characterized in that the step of recording at least one momentary eye image comprises recording a first image containing the iris and the pupil of the eye at a first wavelength of light and recording a second image containing scleral blood vessels at a different second wavelength of light, and that the step of calculating the change of eye position comprises calculating a displacement of the scleral blood vessels between the reference eye image and the second image. As explained above, the first wavelength can be optimized in view of an optimum contrast of the iris/pupil for determining a translational displacement of the eye, whereas the second wavelength can be set such as to optimize the contrast of the scleral blood vessels for determining the rotational displacement. As explained above, the first wavelength therefore preferably corresponds to IR light, and the second wavelength preferably corresponds to a local absorption maximum of hemoglobin.

In a further embodiment of the method according to embodiments of the invention, it comprises the step of extracting scleral blood vessels from the second image, and in still another embodiment it also comprises a step of classifying extracted blood vessels according to their stability and trackability. The subtraction step can be performed as has been described above, i.e. by subtracting the green image from the IR image. Other possible methods comprise selected enhancement/filtering, the use of matched filters and (multi)thresholding, the use of anisotropic filters and (multi)thresholding and in particular accumulated watershed segmentation. The watershed technique has a bias towards fully enclosed features. A method for removing this bias is to artificially add features to the image, such as a black grid, to enhance connectedness or circularity of the features, and then perform the watershed segmentation. The added artificial feature is then removed from the result, leading to a far less biased watershed segmented image. Repeated watershed segmentation with decreasing height level reveals increasingly finer vessels. This provides a stable estimate of the width of the vessels, since wider vessels create deeper valleys in the gray scale image and can be segmented in more height levels.

Criteria for the classification for the detected blood vessels comprise, among others, the question if a feature is a blood vessel and not for example an eye lash or other artifact, and if a blood vessel belongs to the sclera or to the conjunctiva. This classification can be done based on properties of the vessels, such as appearance, location, thickness, focus, connectedness of the vessels, vessel shape direction or contour and intensity/contrast or contrast changes along the length of the vessel. For example, it may be possible to distinguish blood vessels from an eye lash based on the straightness, length and direction (e.g. ±30° from the vertical) or focus of the feature.

As an alternative to the extraction and classification of blood vessels, the method according to the invention can comprise defining an area of interest in the reference eye image and calculating a maximum correlation coefficient between the area of interest and the second image.

According to a further embodiment the present invention deals with the problem of how to locate in an image of an eye those area or areas which contain blood vessels so that these regions can be used for either registration or eye tracking. While there are probably many areas in an eye picture which contain picture elements representing blood vessels, it would be helpful for the purpose of eye tracking or eye registration if one or more regions are chosen where the blood vessels are present in such a manner that they are particularly suitable for tracking or registration.

According to an embodiment of the invention there is provided a method for eye registration or eye tracking based on an initial or reference image and a momentary image, said method comprising: obtaining one or more of so called landmarks in said initial image containing image data which are likely to represent blood vessels or parts thereof; and based on said landmarks, selecting one or more regions of interest as parts of said initial image which are to be used for eye tracking or registration. According to this embodiment the landmark selection makes it possible to select areas (regions of interest) in the initial image which are particularly suitable for tracking or registration.

According to a further embodiment for each of said regions of interest, there is obtained a displacement measurement between said initial image and said momentary image; and if multiple regions of interest are used, said multiple displacement measurements are combined to obtain a final displacement measurement. This makes it possible to take into account that despite the selection of regions of interest which are particularly suitable for tracking, each individual measurement may be erroneous, and by using multiple measurements the accuracy can be increased.

According to a further embodiment the step of obtaining said landmarks comprises one or more of the following:
performing a Fourier transformation based on said initial image and selecting as said landmarks pixels or groups of pixels which have a high intensity in the frequency domain;
convoluting said initial image with one or more templates representing an edge or a corner or a curve in order to select from said convoluted image or images such areas in which edge, corner or curve structures have been detected; or
calculating orthogonal gradients for said initial image and selecting the regions of interest based on said gradients calculated. The aforementioned methods of landmark selection make it possible to perform the landmark selection automatically. This makes it easier for the user to apply the method of the invention. The mentioned methods all give an indication where in the reference image there are contained structures which may be suitable for tracking, in other words they give an indication about where it is likely that blood vessels are present, and based on this indication there can then be selected the regions of interest in an automatic manner which is more convenient than a manual selection of the regions of interest. These methods are based on assumptions about how suitable blood vessels or parts thereof should look like, and the mentioned image processing methods are "sensitive" to such structures and therefore can be used for the automatic extraction of landmarks.

According to a further embodiment of the present invention there is provided a method which first calculates based on an initial or reference image two gradient images for orthogonal gradient directions. These gradient images give an indication of how strong or how steep the image intensity changes along the two orthogonal directions, and they therefore already give kind of a rough indication about the presence of blood vessels because blood vessels are areas where there should be some kind of image gradient in at least one direction.

The method according an embodiment of the invention then further performs a mathematical operation based on that two gradient images which makes sure that there is at least a minimum gradient in both of said orthogonal directions. This makes it sure that there is an image intensity change in both orthogonal directions, this means that there is some certainty that the image structure indicated by these gradients is not just for example a blood vessel extending only into the x- or the y-direction, but rather it is a structure which shows an intensity change (and thereby an image structure) along two orthogonal directions. This is particularly helpful because for the purpose of the detection of rotation angles for eye tracking or eye registration purposes the structure used for registration or tracking must be such that it is not only one-dimensional.

According to a particularly preferred embodiment the mathematical operation which ensures that there is a minimum gradient in both orthogonal directions uses a mathematical approach which ensures that the intensity change is independent from the coordinate system. For that purpose there is used a covariance matrix based on the two gradient images. There is formed a covariance matrix for a certain predefined window around each pixel of the reference image, and based on this covariance matrix the eigenvalues are calculated. These eigenvalues represent the image gradients in two orthogonal directions in a manner independent of the coordinate system, i.e. in a covariant manner.

By taking the minimum eigenvalue for each predetermined window around each pixel of the reference or initial image it can be made sure that the thus selected eigenvalue gives an indication about the minimum gradient of the image in both two orthogonal directions.

The aforementioned method can be applied for all pixels of the reference image, thereby obtaining a minimum eigenvalue for each of the pixels of the reference image, whereas each minimum eigenvalue thus calculated gives a representation about how strong at least the image gradient is in two orthogonal directions. Because especially for the purpose of rotation measurement it is important that the selected features (and the regions of interest selected which contain the suitable features) have gradients in both orthogonal directions to make a rotation measurement possible. This can be achieved by the aforementioned method of using the minimum eigenvalues calculated for each of the pixels of the reference image.

Based on the thus obtained eigenvalue image according to one embodiment one can then select those areas of the reference image which can be assumed that they contain particular suitable structures (blood vessels) for the purpose of tracking or eye registration. These regions (or even individual pixels) may be called landmarks, and they are selected based on the minimum eigenvalue image. For example, one can at first choose which has the maximum eigenvalue among the eigenvalue image pixels, and then define a region of interest around this selected pixel. This will then give the first region of interest for the purpose of eye tracking.

After having blanked out the thus selected pixels of the first region of interest one can again go through the eigenvalue image of the reference image and can select the next highest eigenvalue. Around this pixel one can form a second area of interest, and the procedure may then be repeated either until a suitable number of areas of interest has been obtained, or for example until the eigenvalue corresponding to a certain pixel of the reference image falls below a certain threshold.

Of course it is also possible to imagine other ways of selecting or extracting so-called "landmarks" in the initial image, where said landmarks can be assumed to contain suitable blood vessel structures. One can for example take groups of pixels, e.g. of 5×5 block size from the eigenvalue image, calculate their average intensity, and based on these values select those blocks for which the average intensity is relatively high, e.g. by applying a threshold, by selecting the n blocks with the highest average intensity, or the like.

The thus selected "landmarks then form the base for the "regions of interest" which are then used for a comparison between the reference image and the momentary image for tracking or registration. The regions of interest typically are areas, which are chosen such that they surround the selected "landmarks", e.g. by forming a predefined window around them.

According to a further embodiment one can then use the thus obtained predetermined regions (areas of interest) for the purpose of displacement measurement. For that purpose one compares each area of interest in the reference image with a momentary image to look how much the area of interest must be shifted to find again the area of interest in the momentary image (to look for a "match"). This can for example be done by calculating a correlation measurement for each shifting or displacement value within a certain predetermined window around the region of interest, and this then will lead to a map or an "image" of correlation values where each pixel corresponds to a certain displacement of the reference image and indicates the correlation measurement for this displacement.

According to a preferred embodiment the calculated matching score (the correlation measurement) is further weighted by a weighting value which indicates the "directionality" of features in the reference image like blood vessels. This can for example be done by applying anisotropic steered filters such as a bank of Laplacien of Gausian (LoG) filters. This will then given an indication about the "directionality" of features for each of the pixels of the reference image, and it will kind of "enhance" those structures for which there is a strong directionality like in the case of blood vessels which are long and slim in shape, i.e. have a strong directionality.

Based on the weighting then there is obtained a matching score map for each of the regions of interest, whereas each pixel of the matching score map indicates the matching score for a particular displacement of the reference image based on the correlation value calculated for this shift and weighted with the weighting map.

According to a preferred embodiment the matching scores are then accumulated for the individual displacement values and for the multiple regions of interest to thereby obtain a shift value which is most likely to represent the actual shift value.

This accumulation of multiple matching score maps takes into account and to some extent corrects several effects which may negatively influence the measurement for the individual regions of interest. For example, individual blood vessels may shift their position independently of the eye movement just due to their instability. Moreover, the measurement itself may be erroneous. These effects can be at least to some extent be taken into account and be corrected by accumulating the matching scores for the individual regions of interest.

According to a preferred embodiment furthermore an a priori knowledge about the correlation coefficient and the probability that the eye displacement actually takes the measured value is used to replace the correlation measurement by a corresponding probability. Using this probability thus obtained there is then calculated the accumulated probability for each of the individual displacements based on the multiple regions of interest for which the correlation map has been calculated.

This will then finally give a maximum probability for one of the displacement values which can then be taken as the final displacement value obtained from the measurement.

According to a further preferred embodiment the imposition uncertainty which is introduced by the measurement error is also taken into account by computing for each position the accumulated probability of its neighbors.

According to a further embodiment it is also possible to further classify the selected landmarks or regions of interest according to this suitability for tracking. This can be done by any known classification method or method of supervised learning like neural networks. Such classification techniques or supervised learning techniques may also be themselves used for the selection of the landmarks or regions of interest. This can e.g. be done by successively classifying regions of interest in the initial image using a classifier such as a neural network or any other method of supervised learning and classification.

BRIEF DESCRIPTION OF THE DRAWINGS

Further aspects and advantages of preferred embodiments of the invention will now be illustrated with reference to the accompanying drawings, in which:

FIG. 7 shows a method of displacement measurement according to an embodiment of the invention.

DETAILED DESCRIPTION

Figure 1:
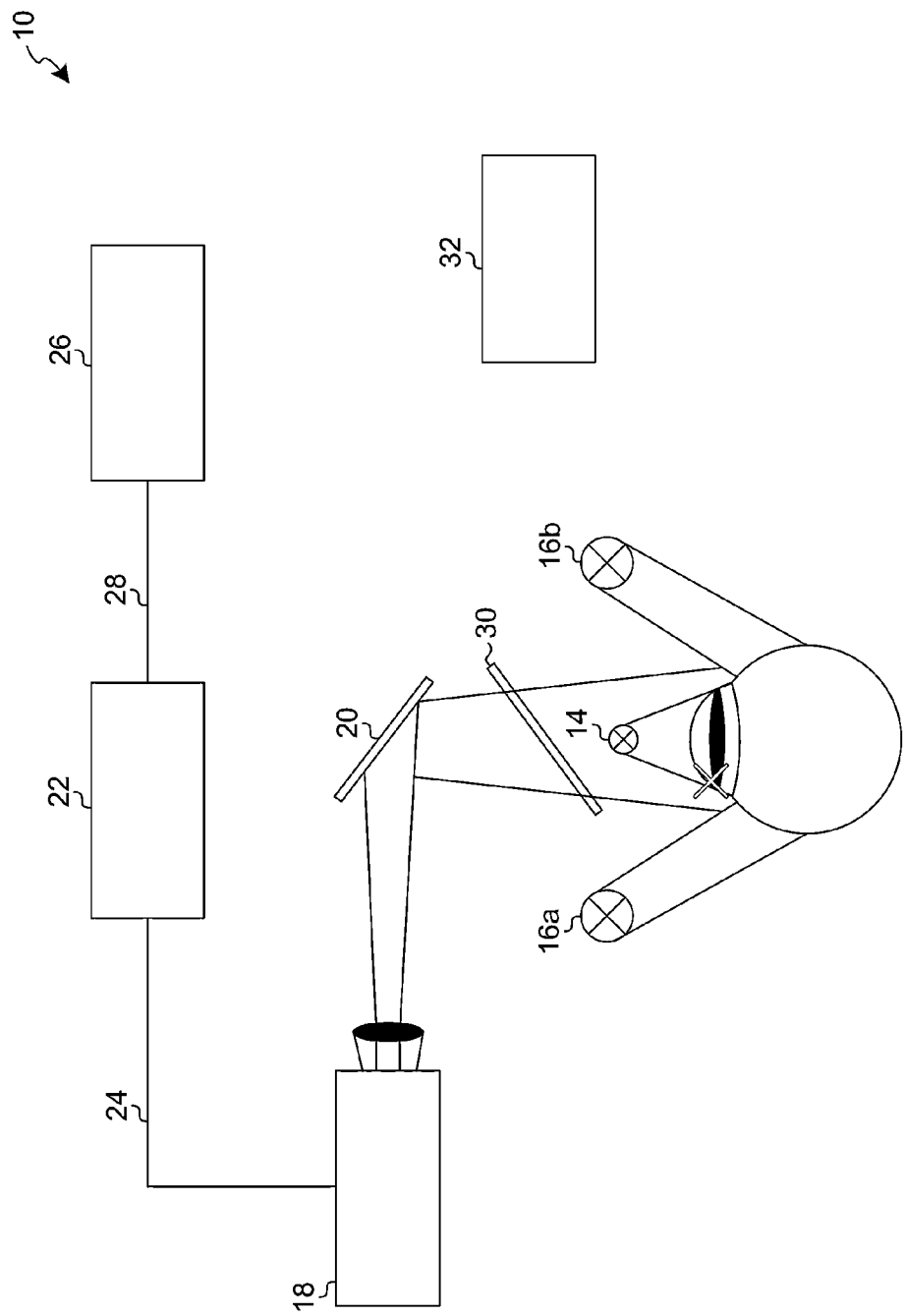
FIG. 1 is a schematic view of an embodiment of the system according to the invention in which the first and second light source systems simultaneously illuminate different parts of the eye.

FIG. 1 shows a first embodiment of a system 10 according to the invention serving for registering and tracking the position of a patient's eye 12.

The system comprises a first light source 14 emitting IR light in the direction of the iris and the pupil of the eye 12. Furthermore the system 10 comprises two second light sources 16*a,b* emitting green light in the direction of the sclera of the eye 12.

As can be clearly seen in FIG. 1, the three light sources 14, 16*a,b* simultaneously illuminate the eye 12: green light from the second light source 16*a* impinges on the left part of the sclera on the left side of the iris, IR light from the first light source 14 simultaneously impinges on the iris itself, and another cone of green light from the second light source 16*b* illuminates the right part of the sclera on the right side of the iris.

The reflections associated to these three cones of light are directed to a camera 18 by means of a movable camera mirror 20. As an example, this camera is a CCD camera having a combination chip with two separate color bands corresponding to the IR light from the first light source 14 and the green light from the second light sources 16*a,b*. In other words, the camera 18 simultaneously takes two pictures of the eye 12, namely an IR image which almost exclusively shows the iris/pupil region, and a green image which almost exclusively shows the sclera of the eye 12 with a particularly sharp contrast of the scleral blood vessels.

Figure 2:
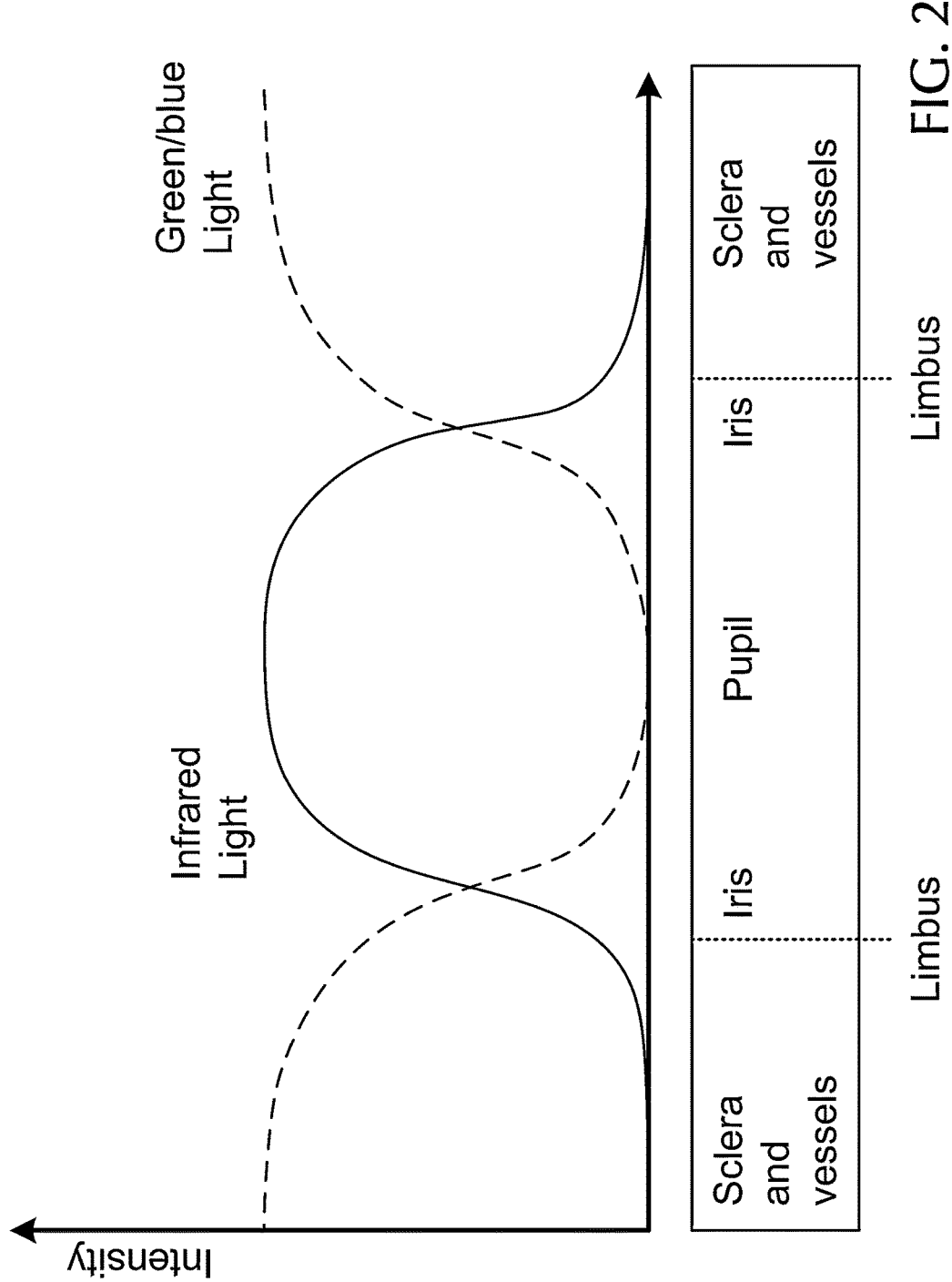
FIG. 2 is a graph illustrating the spatial structure of the beam illuminating the eye in the embodiment according to FIG. 1.

The spatial structure of the light impinging on the patient's eye 12 is shown in FIG. 2 as a graph of light intensity as a function of an eye coordinate. One can clearly recognize the central IR light cone and the two neighboring cones of green (or blue) light impinging on the sclera and its blood vessels.

The camera 18 digitizes the two images made and sends the corresponding information to an image processing system 22 via a data line 24.

The image processing system 22 compares both images to a reference eye image stored in storage means (not shown in the figures). The comparison between the IR image and the reference eye image allows to determine any translational displacements of the eye 12, whereas the comparison between the green image containing the blood vessel positions and the reference eye image allows to determine any rotational displacements of the eye 12, as will be described in detail below.

The image processing system 22 outputs a signal representing the change of eye position to a scanner device 26 via a data line 28. Based on this signal, the scanner device 26 modifies the position of a movable laser mirror 30, which is to reflect a laser beam from a laser 32 to the eye 12 for ablation purposes. With the scanner device 26 correctly controlling the movable laser mirror 30, eye movements detected by the image processing system 22 can be taken into account either for registration or for tracking purposes.

Figure 3:
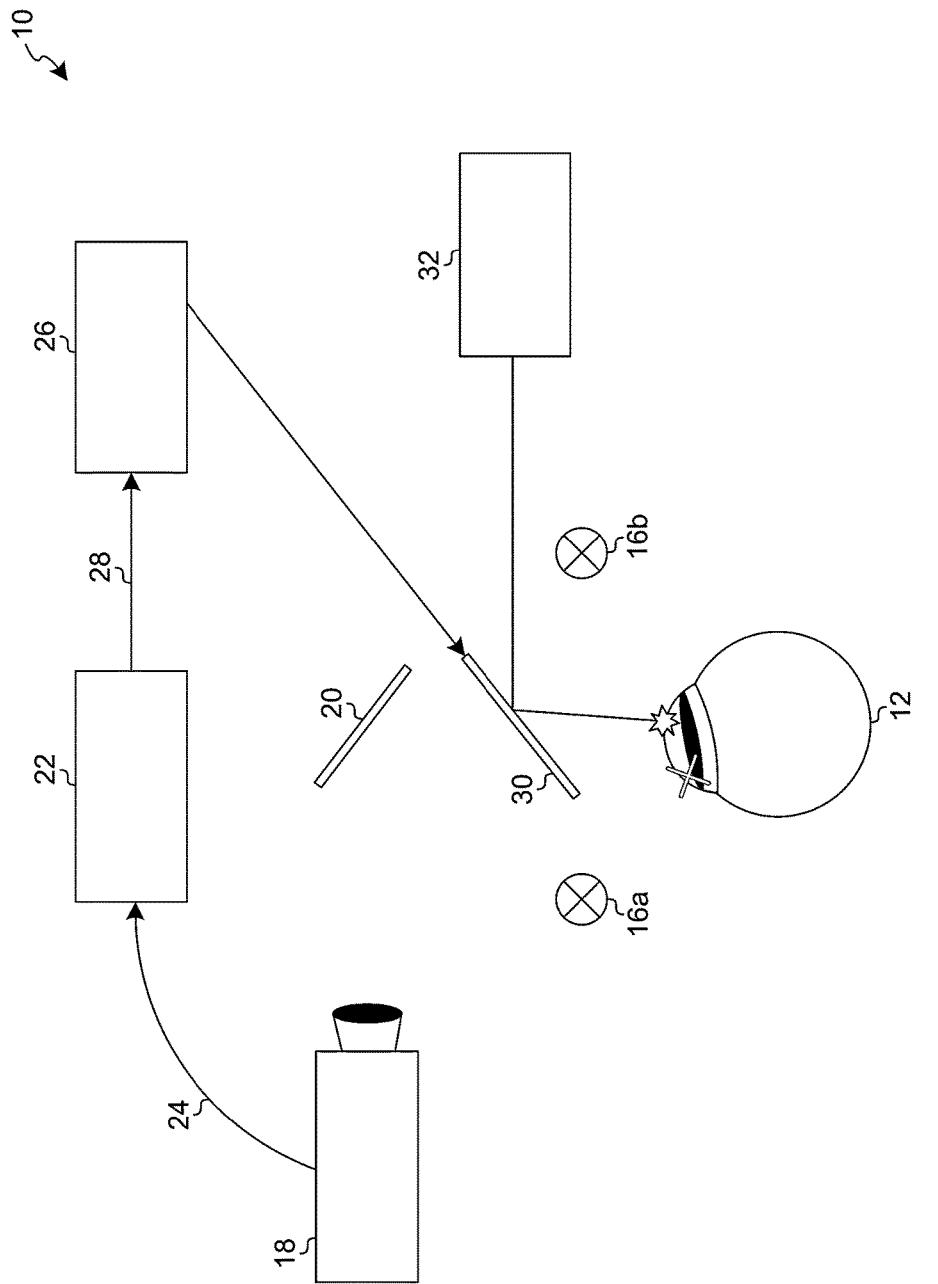
FIG. 3 is a schematic view of the system according to FIG. 1 during corneal ablation.

FIG. 3 shows the system 10 according to FIGS. 1 and 2 during the final step of corneal ablation. The scanner device 26 has slightly tilted the movable laser mirror 30 with respect to its original position in FIG. 1, and the laser 32 emits a laser beam which is reflected towards the eye 12 by the slightly tilted laser mirror 30. The tilt of the mirror 30 compensates for all translational and rotational changes of eye position as schematically indicated by a small rotation of the eye 12 in FIG. 3 with respect to FIG. 1. The IR light source is omitted here for clarity reasons.

Figure 4:
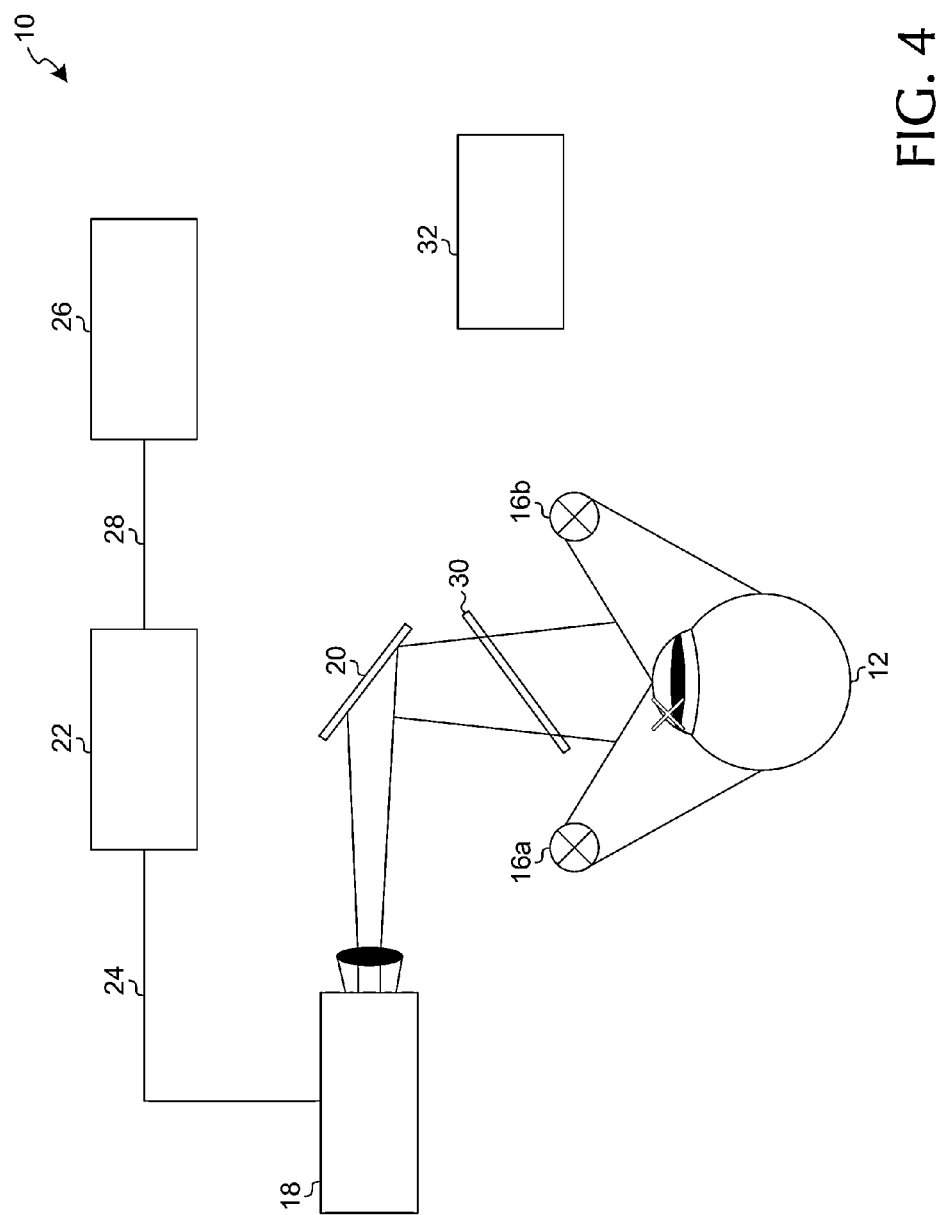
FIG. 4 is a schematic view of a second embodiment of the system according to the invention, in which the two light source systems alternately illuminate the entire eye.

FIG. 4 shows a second embodiment of the system 10 according to the invention. In this second embodiment, the first light source 14 and the two second light sources 16*a,b* alternately illuminate the entire eye. In FIG. 4, the first light source 14 is omitted for clarity reasons. FIG. 4 shows a situation, in which the two second light sources 16*a,b* are active, so that in the situation shown in FIG. 4, the camera 18 only measures a "green" image. As explained above, this image can itself be compared to the reference eye image by the image processing system 22 in order to determine eye rotations based on positional changes of the scleral blood vessels, or the green image made during the situation of FIG. 4 can be subtracted from a preceding IR image in order to yield a difference image which basically only contains blood vessel information. All other components of the second embodiment of the system 10 according to the invention correspond to its first embodiment and will therefore not be described in detail any more.

Hereinafter we will now in somewhat more detail an image processing for the purpose of tracking or registration according to an embodiment of the invention.

Figure 5:
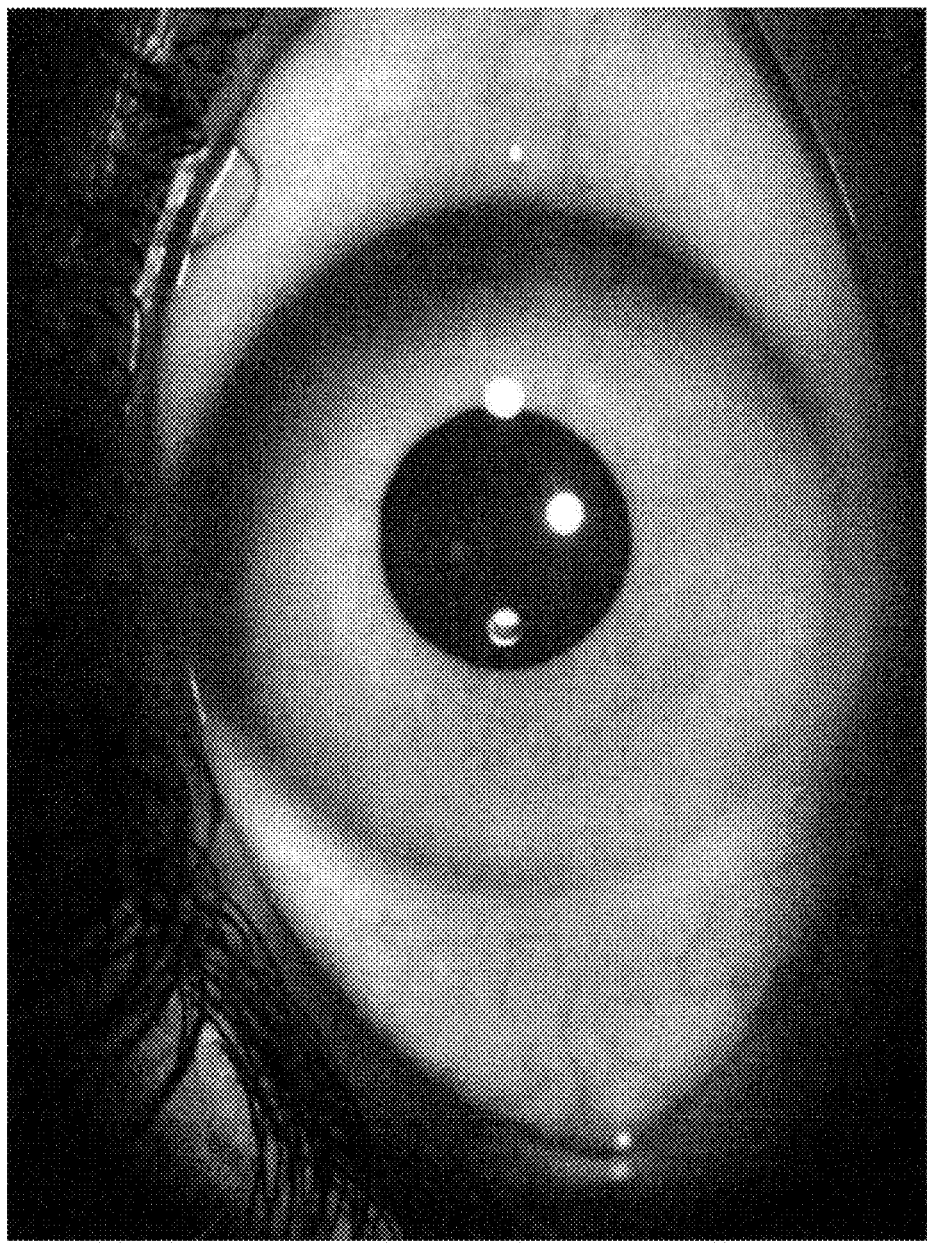
FIG. 5 shows an image of an eye.

FIG. 5 shows an image of the eye which can form the starting point for the method of image processing used in eye registration or eye tracking. The image shown in FIG. 5 may be taken two times, once as a reference or initial image as a starting point, and then later on as a momentary image where the eye has somehow shifted or displaced itself when compared with the reference image.

Assuming that FIG. 5 shows the reference image we will now proceed with the explanation of the method according to an embodiment of the present invention.

First of all there is performed a 2D-centration/registration of the image. This means that at first there is looked for the eye center. This will then later help to extract the scleral area based on the anatomical geometry of the eye, and it furthermore can also be used for the purpose of delivering an initial 2D-translation between the two images (reference image and momentary image).

For the purpose of centration/registration it is assumed that the eye center can be approximated by either the limbus or the pupil center. The pupil center can be calculated using the center of gravity of a convex hull, or object segmented using intensity thresholding or alternatively, though transform or elliptical fit of the edge points. This list of methods is not exhaustive and other techniques well known in the art could be used. The limbus center can be calculated by utilizing the gradient in pixel intensity along a radial line from the pupil center. Using a predetermined gradient threshold, the edge points of the limbus can be found and an elliptical fit algorithm applied to find the limbus center.

Both of these functions are actually auxiliary only for the purpose of blood vessel tracking and rather form an initial starting point for the image processing to be performed later on.

For the purpose of easier image processing and easier calculation of the displacement value there is then next performed a polar coordinate transformation. In particular for the purpose of torsion measurement the transformation into polar coordinates is very helpful because it makes the calculation much easier. As a matter of course this transformation relies on a correct identification of the eye center. However, inaccuracies in the center can be compensated at the end of the processing, as they are easily detectable by inaccuracies in 2D registration (equal torsion values of contrary sign) on the left and right side of the image. The transformation can for example be performed for image areas which are situated on the left and the right side of the iris in an approximated range of $$\theta \times R = [-pi/4 : pi/4] \times [6 \text{ mm}:11 \text{ mm}]. \quad (1)$$

In the transformation bilinear interpolation is used as known to the person skilled in the art. Any pixels which fall outside the image space are defaulted to zero.

It should be noted that if hereinafter x,y-coordinates are mentioned, that then this may either relate to cartesian coordinates or to polar coordinates, the latter actually being more practical especially for torsion measurement.

As a further preparation step the invalid regions of the eye image are marked or masked. First of all the so-called cornea reflections are detected. These are spots in the eye which are particularly bright, much brighter than the surrounding areas. To find and mark or mask those areas the following approach can be taken.

First of all a median filter is applied to the image as follows:

$$I \xrightarrow{20 \times 20 \ filter} I_{median} \quad (2)$$

Next the difference between the median image and the reference is calculated:

$$I_{diff} = I - I_{median} \quad (3)$$

As a next step then there are found those locations for there exists a high difference (with T as a fixed parameter):

$$\{X,Y\} = \{(x,y) | I_{diff}(x,y) > T\}, \quad (4)$$

Those pixel locations thus found can be assumed to be corneal reflections and they have to be either taken out or "smoothed out". This can for example be done by replacing the found pixel with non-corrupted values by the following approach:

$$I(X,Y) = I_{median}(X,Y) \quad (5)$$

As a next step then there is performed a masking step which segments the valid regions, i.e. selected regions within the sclera area. It can be assumed that the vessels in the sclera region are on a white background and therefore the contrast is relatively high.

In order to extract or segment the scleral region the following method can be used. First of all, it is assumed that the scleral region has a better reflectivity than the eye lids. This means that the eye lid-sclera border then creates gradients in the image. As a consequence, the brightness varies spatially, and based on this initial assumption the scleral region can be extracted by the following method.

First of all there is computed a global weighted image mean with stronger emphasis on gradient points:

$$Val_{global} = \text{mean}(I^* \text{grad}(I)),$$

$$Grad_{global} = \text{mean}(\text{grad}(I)) \quad (6, 7)$$

Thereby grad(I) is some gradient operator, such as steerable LoG filters. A particular embodiment of such a filter will later on be described in more detail.

Then the image is divided into a set of non-overlapping subregions (e.g. 3×3 pixels), and then for each region the same parameter as mentioned in equations (6) and (7) is calculated:

$$Val_{local} = \text{mean}(I_{local}^* \text{grad}(I_{local})),$$

$$Grad_{local} = \text{mean}(\text{grad}(I_{local})) \quad (8, 9)$$

Next then there is a threshold applied for each subregion $$T = \frac{Val_{global} + \alpha * Val_{local}}{Grad_{global} + \alpha * Grad_{local}}$$

α thereby is a predefined parameter for weighting the influence of the local statistics.

Based on the threshold then there can be decided whether the corresponding pixel belongs to the sclera or not, and depending on that it is either a sign a 0 or a 1 thereby forming a mask which masks the non-scleral region.

Assuming that some of morphological irregularities may occur during the before mentioned procedure, these spurious regions or holes may be eliminated by suitable morphological operations such as opening and closing.

Moreover, the morphological operations may be applied to eliminate the border pixels close to eye lids and limbus. These morphological operations of opening and closing and erosion are know to the person skilled in the art and therefore are not further described here.

Based on the foregoing operations now there has been obtained a mask which masks the scleral region as the starting point for the further procedure.

The next step then relates to the finding of those parts of the scleral region which contain image features which are particularly suitable for image tracking. This means that those pixels or groups of pixels have to be found where image information about blood vessels is not only present but also is present in a manner which is particularly suitable for tracking. The result of this step will be that several so-called landmarks have been found where one can assume that the corresponding image information in the reference image not only is related to the presence of blood vessels but also is in a manner which makes it suitable for image tracking and registration.

This step of the method of the present embodiment is based on the assumption that a good tracking quality can be obtained only if the landmark has significant gradients on orthogonal directions. It is therefore at first based on the initial reference image applied a gradient operator which leads to two gradient images, one in each orthogonal direction. This step can be mathematically expressed as follows:

$$I \xrightarrow{Sobel(7 \times 7)} \{G_x, G_y\} \quad (11)$$

Two resulting gradient images then give a first indication about the gradients of the reference image in orthogonal directions. However, according to the method of the present embodiment not only the gradient in one direction is decisive, but rather the particularly good area for image tracking should have significant gradients in both orthogonal directions. It therefore is looked for image parts where the gradients in both orthogonal directions are significant.

According to one possibly embodiment one could for each of the pixels of the gradient images look for the minimum of the two gradient values, and use this minimum value as the pixel value for a resulting final "minimum gradient image". Then each pixel in this final minimum gradient image would represent the minimum gradient in the two orthogonal directions for each pixel of the reference image.

However, according to a particularly preferred embodiment there is used a slightly different approach which uses a covariant expression taking into account the two gradient images. For that purpose there is for each of the pixels of the reference image formed a covariance matrix over a block of size of 32×32 pixels centered in each pixel of the reference image. This can be mathematically expressed as follows:

$$H = \begin{pmatrix} \sum G_x G_x & \sum G_x G_y \\ \sum G_x G_y & \sum G_y G_y \end{pmatrix} \quad (12)$$

The covariance matrix then is a formulation which is coordinate system independent and which nevertheless takes into account the image gradients into the two orthogonal directions over a block surrounding each pixel of the reference image by a certain predetermined size.

As a next step then there are computed the eigenvalues of the covariance matrix H, and for each of the pixels of the reference image there are thus obtained two eigenvalues. To obtain a final image representing the quality of the gradients involved direction (the final gradient image) or quality image $I_{quality}$ there is then chosen for each of the pixels the minimum eigenvalue corresponding to the matrix which corresponds to this pixel. This can be mathematically expressed as follows:

$$I_{quality}(x,y) = \min(\lambda_1^{x,y}, \lambda_2^{x,y}) \quad (13)$$

The thus obtained quality representing image is an indication for each of the pixels of the reference image as to how strong there are the gradients, or better to say, the minimum gradient in two orthogonal directions in this image point. For those pixels where this value is particularly high, it can be assumed that this is a good image part which contains image features suitable for tracking. Therefore, at first there is chosen the maximum value of this image as a starting point for a first region of interest suitable for tracking. This can be done as follows:

$$\text{Max} V = \max(I_{quality}) \quad (14)$$

This maximum value then gives a first landmark or a first image part where one can assume that there are features suitable or particularly suitable for image tracking.

One can then draw a region of interest as a predetermined window surrounding the thus found landmark.

Then there is conducted a search for further landmarks. This can for example be done by looking for other pixels in the quality image where the pixel value is high, for example the next highest value from the maximum. In order to make sure that the thus obtained next landmark is not too close to the initially obtained value there are first at all neighbours of the initial maximum value set to 0, for example on a range of a minimum distance of 16 pixels. Then there is looked for the next maximum value in the quality image.

Figure 6:
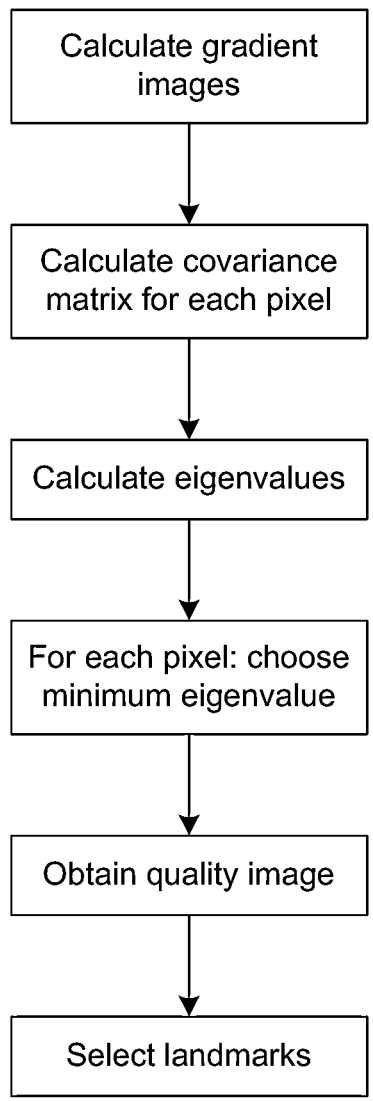
FIG. 6 shows a process flow according to an embodiment of the invention.

The aforementioned procedure is briefly explained as a flow chart in FIG. 6. First of all the two gradient images are calculated, then there is calculated the covariance matrix for each pixel of the reference image based on the two gradient images. Then based on the covariance matrix the eigenvalues are calculated, and then for each pixel of the reference image there is chosen the minimum eigenvalue to obtain a quality image representing the "feature quality" with respect to its suitability for the purpose of image tracking. Based on the thus obtained quality image there are selected picture elements or regions as landmarks which are suitable for image tracking. A "landmark" therefore may be a pixel selected from the quality image, or it may be an area surrounding a pixel selected from the quality image, or it may be an area selected from the quality image. In the embodiment described hereinafter a landmark is a pixel and the region of interest is an area surrounding it, however, the region of interest may as well be directly selected based on the quality image for example as an area having the highest average intensity.

Assuming that the selected landmark is a pixel in the quality image, then for each of the thus selected landmarks there is chosen a corresponding region of interest, for example by selecting a predefined surrounding area for each landmark. This region of interest is then the basis for the calculation of a correlation factor between the reference image and the momentary image taken at a later stage. For that purpose it is looked then later how much the region of interest has to be shifted of displaced from its position in the reference image to match with its position in the momentary image. The most easy approach would be to just calculate the difference value between the region of interest at the momentary image and the reference image for each possible displacement value. Because the possible movement of the eye is somewhat limited, there can however be set a predetermined area (a kind of a "displacement window" surrounding each region of interest within which one can assume that the eye movement should be. For this predetermined region or displacement window there can then be calculated the difference between the momentary image and the reference image for the region of interest for each possible displacement value. This is schematically illustrated in FIG. 7. Within the eye 1200 in the reference image there is defined a predetermined window (displacement window) 1210 within which the region of interest 1220 determined based on the landmark extraction can move. For the momentary image 1250 there are then within the predetermined region (the displacement window) 1260 calculated differential images for each possible displacement of the region of interest 1270. This is indicated schematically by the dashed versions of the regions of interest 1270.

This then results in a differential image for each possible displacement (within the displacement window), and for the actual displacement one could for example use such a displacement value for which the differential image forms a minimum, e.g. by adding up all pixels of the differential image and looking for the displacement value for which this sum is the minimum.

While this would be quite a simple approach, according a preferred embodiment of the present invention, a more sophisticated approach can be taken.

At first, according to a preferred embodiment the landmarks found by the method explained before are not the only input for the calculation of the final correlation value. Rather, there is a further input which is based on the assumption that those areas of the reference image where blood vessels are present should be weighted more heavily in calculating the final correlation value.

For that purpose first of all there is calculated a weighting map which assigns a weight for each of the pixels of the reference image. Those pixels or areas where blood vessels are present should be weighted more heavily than other areas.

Assuming that vessels are dark thin bandlike structures with clear directionality, one can find these vessels or find a presentation of the image where they show up as enhanced features by applying an operator which enhances these features. One example for such a directionality enhancing operator is a bank of LoG anisotropic steerable filters.

In a preferred embodiment of the present invention five filters are used with equidistant orientation in [0:pi/2] range. The used standard deviations for the gaussians are $\sigma_d$, $\sigma_s$=1.5, 3, where d stands for derivation and s for smoothing.

The image may then be applied to the filter band as follows:

$$F_i = I \otimes \text{LoG}_i, \text{ for } i=1:5 \qquad (15)$$

The output of the application of the filter may then be used as the min/max difference as follows:

$$FM(x,y) = \max_i(F_i(x,y)) - \min_i(F_i(x,y)) \qquad (16)$$

Thereby the base LoG filter (of orientation 0) is given by:

$$\text{LoG}(\theta = 0) = g(x) * \frac{\partial^2 g(y)}{\partial y^2},$$

where g is the Gaussian function (17)

The steered filters are obtained by rotating the base version by an angle θ:

$$\text{LoG}(\theta) = \text{rot}_\theta(\text{LoG}(0)) \qquad (18)$$

This then results in an image which is a kind of feature image or a feature map, where for each pixel of the reference image there is obtained a weighting value which lies between 0 and 1 and which is an indication as to how likely it is that the pixel contains or belongs to a blood vessel.

Based on the found landmarks and the found weighting map (the feature map) one can then initiate the landmarks used for image tracking. As mentioned already before the landmarks are extracted based on the covariance matrix and its eigenvalues, and then for each selected landmark there is defined a region on interest surrounding it. This results in a multiple regions of interest, and for each of them within a displacement window a displacement measurement is performed.

For each of these multiple regions of interest there is then obtained the corresponding feature map or weighting value map. As another alternative one can before performing the actual matching calculate the feature map, one then further can calculate the landmarks and their surrounding areas (regions of interest), and these regions of interest are the areas for which the actual matching is to be performed. These regions of interest therefore are "templates" which actually define the areas within which the actual reference image and the feature map (weighting map) are used for displacement measurement, and they therefore may be stored as templates in advance after their calculation based on the initial image. For the area of the templates then later the correlation value is calculated for such displacement values where the templates are within a certain predefined window (displacement window).

These two images or templates (one for the actual reference image, one for the feature map) corresponding to the multiple regions of interest therefore form the input for the actual matching process.

The matching process itself is now described in more detail in the following.

Figure 8:
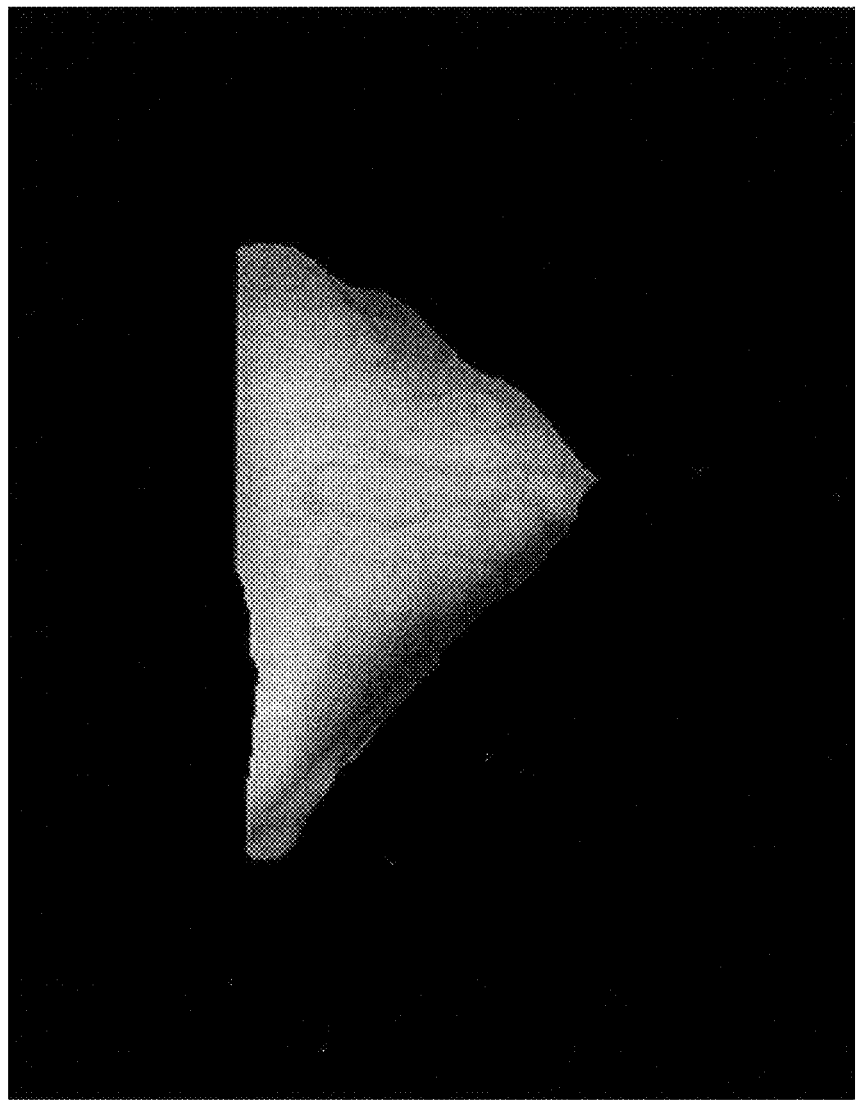
FIG. 8 shows scleral blood vessels in an initial image.
Figure 9:
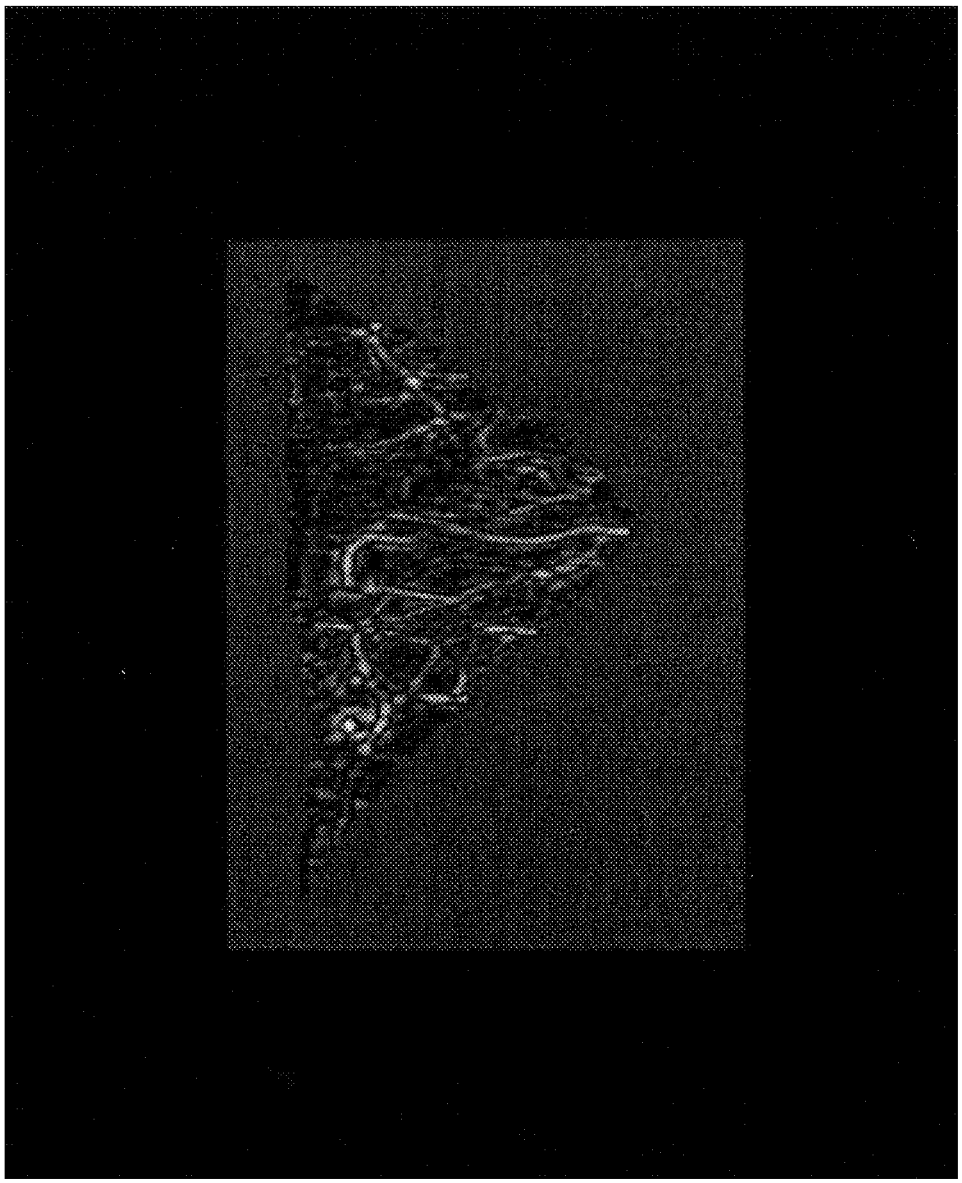
FIG. 9 shows the feature map corresponding to the image of FIG. 8.

FIG. 8 shows as an example a fraction of the reference image containing blood vessels, and FIG. 9 shows as an example the weighting image or feature map obtained from the part of the reference image by using the before mentioned method. It can be seen that in the weighting image the blood vessel structures clearly are enhanced and therefore heavier weight will be given to the blood vessel structures when calculating the final correlation measure.

For the purpose of eye registration or eye image tracking there has to be calculated a displacement value which indicates how much the momentary image is displaced from the original reference image. This displacement value is calculated based on the regions of interest which have been obtained based on the extraction of the landmarks.

For each of the regions of interest there has been obtained by the landmark extraction there is defined a surrounding area (a displacement window) for example as follows. To the left and to the right the surrounding area is 10 pixels wider than the region of interest obtained by the landmark extraction. In the vertical direction the predetermined area the predefined area is for example so many pixels higher than the corresponding block as is represented by 15° to each side. Assuming that the selected landmark is a block of 32×32 pixels, then this results in a predefined window of 52 pixels in width and 152-162 in height.

The region of interest obtained based on the landmark extraction then is used as a template and is shifted within the predefined area (the displacement window) such that it still completely lies inside it.

Figure 10:
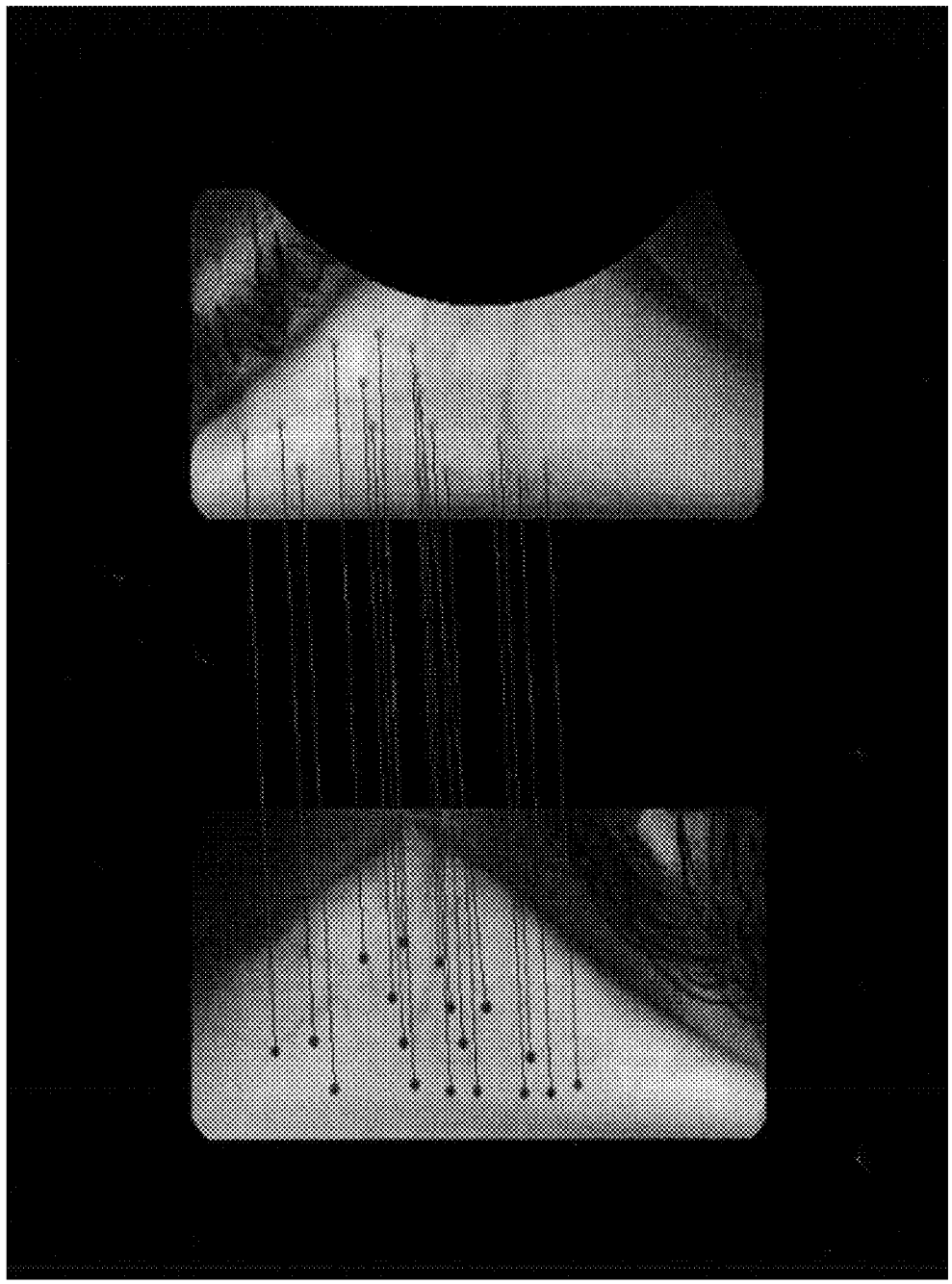
FIG. 10 shows illustratively landmarks in an initial image and a momentary image.
Figure 11:
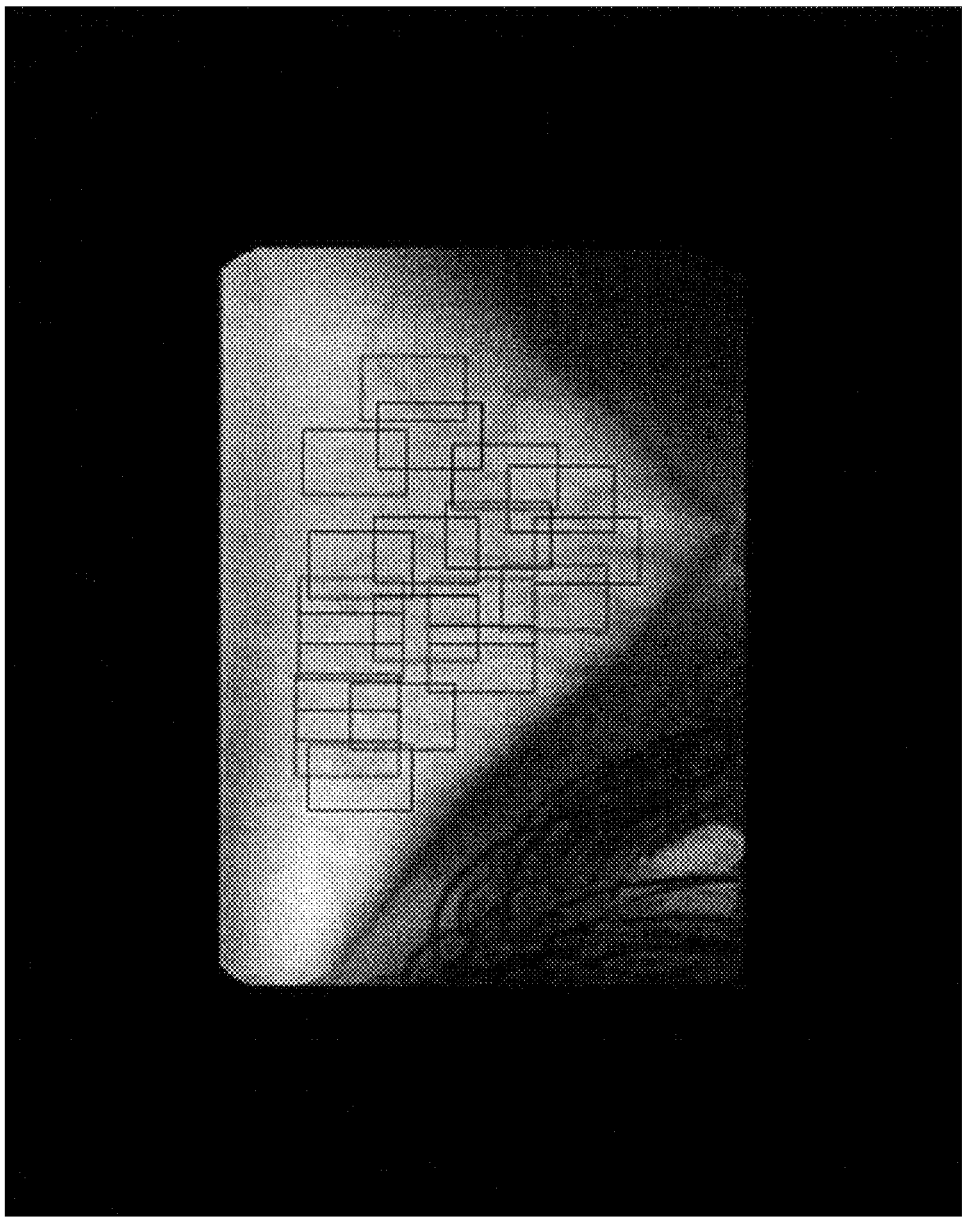
FIG. 11 shows the predetermined regions respectively surrounding the Landmarks of FIG. 8.

For each of the templates there is then performed a matching between the initial image and the momentary image. This is schematically illustrated in FIG. 10. FIG. 10 shows the landmarks in the initial image (left) and the momentary image (right). FIG. 11 then illustrates that the actual matching is performed for regions of interest which surround the landmarks. These are shown as rectangles in FIG. 11.

Then the matching between the template and the underlying block of the momentary image ($B_{xy}$) is computed as follows:

$$MS(x,y) = ms(T_{image}, T_{weight}, B_{xy}), B_{xy} \subset ROI \quad (19)$$

Thereby MS(x, y) represents a matching score function which is described below.

Assumed that $T_{image}$ is the image part of the reference image which corresponds to the selected region of interest based on the landmark extraction. Furthermore, assumed that $T_{weight}$ is the corresponding part of the weighting image (the templates). Then the procedure is as follows.

First of all $T_{image}$ is normalized and also B is normalized. Thereby B is the momentary image.

Then there is computed a weighted statistics for $T_{image}$ based on $T_{weight}$. This is then by computing usual statistics taken into account the importance of each pixel. This can be mathematically described as follows:

$$m_w = \frac{1}{N} \sum_{x,y} I(x, y) * W(x, y) \quad (20)$$

$$std_w = \frac{1}{N} \sum_{x,y} |I(x, y) - m_w| * W(x, y) \quad (21)$$

Next then there is computed the contrast as follows:

$$c = std_{Tweight}(T_{image})/std_{Tweight}(B) \quad (22)$$

Then there is computed the difference image between the momentary image B and the reference image $T_{image}$ by taking into account the statistics as follows:

$$I_{diff} = c*(B - m_{Tweight}(B)) - (T_{image} - m_{Tweight}(T_{image})) \quad (23)$$

Then there is computed the matching score as:

$$m_{pq} = \sum_{x,y} x^p x^q I(x, y) \quad (24)$$

The normalization of the images mentioned before has the purpose of removing the illumination differences. It is based on the assumption that the illumination differences can be approximated to planer surfaces. The normalization is performed as follows:

First of all the algebraic moments of the orders $m_{00}$, $m_{01}$, $m_{10}$ for a given image are calculated as follows:

$$m_{pq} = \sum_{x,y} x^p x^q I(x, y) \quad (25)$$

Then the contribution of the corresponding polynomials is subtracted:

$$I_N = I - \sum_{p,q} m_{pq} P_{pq} \quad (26)$$

Where the used polynomials are $$P_{00}=1, P_{10}=x, P_{01}=y \quad (27)$$

The resulting matching score gives for each displacement value of the region of interest within the predefined window a corresponding matching score and thereby it results in a matching score map, where each pixel element corresponds to a displacement value.

Such a matching score map is obtained for each of the regions of interest (each template) which have been obtained by the landmark extraction.

This means that there has been obtained a plurality of maps of matching scores, each map corresponding to a certain region of interest, and each giving an individual estimate for a certain displacement value which lies within the predefined window (displacement window).

In the next step these matching scores or matching results are aggregated or accumulated to obtain a final matching score for the individual displacement values to then obtain a final displacement value. This is carried out based on the assumption that the measurement of the displacements is influenced by measurement errors, moreover, there is also probably an influence of unstable blood vessels. These influences when accumulating the individual measurement results should cancel out, and by using the most likely measurement result one should get a good approach for the actual displacement value.

Therefore, there is followed a maximum likelihood approach for the torsion a kind of an optimum estimator.

First of all the individual matching scores are transformed into corresponding probability values. This is based on an a priori knowledge about the correspondence between the probability of a matching score and a certain probability that the displacement actually takes this value. In other words, there is a relation between the matching score distribution and the probability distribution which possesses in each point of a likelihood that the feature is in that position or in the small neighborhood of it.

This means that a statistical correlation exists between the matching score and the feature presence in a given location. However this correlation is loose, in the sense that no matching score can guarantee either the presence or the absence of the feature in a particular location. The type of disturbances for the matching score actually fall into two large categories: First of all the imprecision, i.e. the matching score in the correct position may be smaller than the one of one or more points on the neighborhood of the valid position. Another imprecision results from outliers, i.e. the matching score in the correct position is smaller than one or more points arbitrarily far from the valid position.

Based on the assumptions there is constructed an a priori knowledge about the conditional probability of a matching score under valid detection p(s/v). This probability function may be obtained experimentally, and it can either be stored in the look up table or it can be approximated by an analytical function. In the present embodiment the later is used as follows:

$$p(s/v) = \max\left(a \frac{(2-s)}{\alpha^2} \exp\left(-\left[\frac{1-s}{\alpha}\right]^2\right), p_{outlier}\right) \quad (28)$$

Thereby $p_{outlier}$, is the amount of probability that cannot be dismissed by any value of the matching score. Based on this correlation the matching score map is then transformed into a probability map using the above relation (28) as follows:

$$P_i(x,y) = p(MS_i(x,y)), \text{ where } i \text{ is the index of landmark} \quad (29)$$

Then the probability map is normalized so that $$\sum_{x,y} P_i(x,y) = 1 \quad (30)$$

The matching score map therefore is transformed into a probability field as follows:

$$MS_i \rightarrow PF_i \quad (31)$$

The probability fields of each side of the iris (left and right side):

$$Acc_L = \sum_{i \in L} PF_i, Acc_R = \sum_{i \in R} PF_i \quad (32)$$

It should be noted here that the "mathematically correct" implementation should be $$Acc_L = \prod_{i \in L} PF_i, Acc_R = \prod_{i \in R} PF_i \quad (33)$$

However, for convenience reasons the version shown in equation (32) is used. Then there is determined the maximum value and the maximum location in each accumulator, where s is the side (left or right from the iris):

$$\langle x_M^S, y_M^S, p_M^S \rangle = \{x,y, Acc_S(x,y) | Acc_S(x,y) = \max(Acc_S)\} \quad (34)$$

The actual displacement is obtained by taking into account just the location of the maximum.

Assuming that we are calculating in polar coordinates, and further assuming that the vertical coordinate (y) corresponds to the torsion, then the torsion can be determined by taking into account the vertical position of the maximum location:

$$y_M^L \rightarrow T_L, y_M^R \rightarrow T_R \quad (35)$$
$$W_L = p_M^L, W_R = p_M^R$$

If $|T_L| - |T_R| > 1.5$ deg then one may pick the most credible value (based on $W_R$, $W_L$)
If not, then $$T = \frac{W_L T_L + W_R T_R}{W_L + W_R}, \quad (36)$$

The confidence may be computed as:

$$W = \frac{1}{2}(W_L + W_R) \quad (37)$$

When calculating the probability field the imposition uncertainty may be included by computing for each position the accumulated probability of its neighbors:

$$PF_i(x^c, y^c) = \sum_{x,y} P_i(x,y) \exp\left(-\frac{(x-x^c)^2 + (y-y^c)^2}{\sigma_{local}}\right), \quad (38)$$

for every $x^c, y^c$, thereby the parameter σ is controlling the local uncertainty (for example σ=3)

With the foregoing embodiment it is possible to calculate a displacement value which is not only based on the single part of the image but rather on multiple image parts. The multiple regions used for displacement calculation are based on landmark extraction, i.e. they have been selected such that based on the features they contain are particularly suitable for the purpose of eye registration or image tracking.

By using a correlation value which is computed by further taking into account a weighting map it is made sure that those image areas where blood vessels can be assumed to be present are particularly weighted and therefore this enhances the correctness of the final result.

Moreover, by accumulating the multiple correlation values for the multiple regions of interest measurement errors and effects due to instability of blood vessels are cancelled out, or in other words, by taking the most likely displacement value the effect of these negative influences can be kept small such that finally there is obtained a good displacement value and eye registration or eye tracking can be performed very well.

It will be clear to the skilled person that the aforementioned description explained the invention by means of illustrative embodiments and that changes can be made without departing from the invention.

The invention claimed is:
1. A method for registering or tracking an eye, the method comprising:
   recording an initial image of a patient's eye in a reference position;
   obtaining a landmark in the initial image, wherein the landmark corresponds to image data of the initial image that represents blood vessels or parts thereof;
   based on the landmark, selecting a region of interest as part of the initial image which is to be used for eye tracking or registration;
   performing a displacement measurement for the region of interest to obtain a displacement between the initial image and a momentary image of the patient's eye, wherein performing the displacement measurement comprises:
   recording the momentary image of the patient's eye;

calculating a change of eye position between the initial image and the momentary image; and outputting a signal representing the change of eye position;

wherein:

recording the momentary image comprises recording a first image containing the iris and the pupil of the eye at a first wavelength of light and recording a second image containing scleral blood vessels at a different second wavelength of light; and calculating the change of eye position comprises calculating a displacement of the scleral blood vessels between the initial image and the second image.

* * * * *